US006855307B2

(12) United States Patent
Shane et al.

(10) Patent No.: US 6,855,307 B2
(45) Date of Patent: Feb. 15, 2005

(54) PRESSURIZED SOLUTION FEED SYSTEM FOR INTRODUCING HYPOCHLOROUS ACID TO A FLUID STREAM

(75) Inventors: Tommy J. Shane, Loganville, GA (US); Harvey Swain, Lawrenceville, GA (US)

(73) Assignee: Tomco2 Equipment Company, Loganville, GA (US)

( * ) Notice: Subject to any disclaimer, the term of this patent is extended or adjusted under 35 U.S.C. 154(b) by 376 days.

(21) Appl. No.: 10/050,491

(22) Filed: Jan. 16, 2002

(65) Prior Publication Data

US 2002/0134731 A1 Sep. 26, 2002

Related U.S. Application Data

(60) Provisional application No. 60/261,923, filed on Jan. 16, 2001, and provisional application No. 60/316,047, filed on Aug. 30, 2001.

(51) Int. Cl.[7] ............................................. C01B 11/04
(52) U.S. Cl. ........................................ 423/473; 423/474
(58) Field of Search ............................ 423/472, 473, 423/474; 210/724; 261/DIG. 7

(56) References Cited

U.S. PATENT DOCUMENTS

| | | | |
|---|---|---|---|
| 3,958,020 A | 5/1976 | deVries | |
| 4,017,592 A | 4/1977 | Penard et al. | |
| 4,146,578 A | 3/1979 | Brennan et al. | |
| 4,147,761 A | 4/1979 | Wojtowicz et al. | |
| 4,190,638 A | 2/1980 | Hoekje et al. | |
| 4,244,978 A | 1/1981 | Barta | 426/332 |
| 4,250,144 A | 2/1981 | Ratigan | 422/112 |
| 4,313,827 A | 2/1982 | Ratigan et al. | 210/136 |
| 4,333,833 A | 6/1982 | Longley et al. | 210/198.1 |
| 4,362,753 A | 12/1982 | Barta | |
| 4,391,775 A * | 7/1983 | Huber et al. | 422/82.03 |
| RE31,348 E | 8/1983 | Wojtowicz et al. | |
| 4,504,456 A | 3/1985 | Yant et al. | |
| 4,578,119 A | 3/1986 | Marcus et al. | 134/4 |
| 4,769,154 A | 9/1988 | Saylor | 210/707 |
| 4,801,353 A | 1/1989 | Mason | |
| 4,996,741 A | 3/1991 | Covell | 452/74 |
| 5,037,627 A | 8/1991 | Melton et al. | |
| 5,118,426 A | 6/1992 | Duncan et al. | |
| 5,120,452 A | 6/1992 | Ness et al. | |
| 5,165,910 A | 11/1992 | Oikawa et al. | |
| 5,178,579 A | 1/1993 | Simmons | 452/123 |
| 5,234,703 A | 8/1993 | Guthery | 426/331 |
| 5,322,677 A | 6/1994 | Shaffer et al. | |
| 5,364,650 A | 11/1994 | Guthery | 426/331 |
| 5,487,835 A | 1/1996 | Shane | |
| 5,514,264 A | 5/1996 | Shane | |
| 5,720,438 A * | 2/1998 | Devine et al. | 241/21 |
| 5,935,518 A | 8/1999 | Richard et al. | 422/28 |
| 6,019,905 A | 2/2000 | Waggoner | 210/739 |
| 6,083,095 A | 7/2000 | Simmons | 452/123 |
| 6,093,093 A | 7/2000 | Mostoller et al. | 452/173 |
| 6,220,952 B1 | 4/2001 | Taylor et al. | 452/173 |
| 6,455,086 B1 * | 9/2002 | Trinh et al. | 426/321 |
| 6,605,308 B2 | 8/2003 | Shane et al. | 426/332 |

FOREIGN PATENT DOCUMENTS

| | | |
|---|---|---|
| GB | 1 428 920 | 3/1976 |
| WO | WO99/36364 | 7/1999 |

OTHER PUBLICATIONS

Emswiler–Rose, B., Kotula, Anthony W. (1984) Inhibition of Bacterial Growth by Two ChlorineSources in a Model System, Journal of Food Science, vol. 49, p. 931–933, no month.

Odlaug, Theron, Pflug, Irving J. (1978) Microbiological and Sanitizer Analysis of Water Used for Cooling Containers of Food in Commercial Canning Factories in Minnesota and Wisconsin, Journal of Food Science, vol. 43, p. 954–963, no month.

Johnson, M.G., et al. (1979) Bacterial Counts on Surfaces of Carcasses and in Ground Beef from Carcasses Sprayed or Not Sprayed with Hypochlorous Acid, Journal of Food Science, vol. 44, p. 169–173, no month.

Ghanbari, H.A. et al. (1981) The Fate of Hypochlorous Acid During Shrimp Processing: A Model System, Journal of Food Science, vol. 47, p. 185–197, no month.

Romans, John R., Ziegler, P. Thomas (1977) The Meat We Eat, p. 22–23, 56–57, 118–119, 124–125, 197–200., no month.

* cited by examiner

*Primary Examiner*—Ngoc-Yen Nguyen
(74) *Attorney, Agent, or Firm*—Todd Deveau; Thomas, Kayden, Horstemeyer & Risley:LLP

(57) ABSTRACT

A system and method are disclosed for increasing the concentration of hypochlorous acid in a quantity of water. Acid is injected into chlorinated water to decrease the pH of the chlorinated water. By decreasing the pH, the hypochlorite/hypochlorous acid equilibrium of the chlorinated water is shifted to increase the concentration of hypochlorous acid on the treated water.

18 Claims, 3 Drawing Sheets

PRESSURIZED SOLUTION FEED SYSTEM FOR INTRODUCING HYPOCHLOROUS ACID TO A FLUID STREAM

RELATED US APPLICATION DATA

This application claims priority from U.S. Provisional Application No. 60/261,923 filed Jan. 16, 2001, and U.S. Provisional Application No. 60/316,047 filed Aug. 30, 2001, both incorporated herein by reference.

BACKGROUND OF THE INVENTION

1. Field of the Invention

This invention relates generally to the field of disinfectants, and relates more specifically to a method and apparatus for producing hypochlorous acid solutions and maintaining hypochlorous acid concentrations by manipulating the pH of the solution. In particular the invention relates to the use of acids to produce or maintain hypochlorous acid levels in aqueous solutions.

2. Background of the Invention

Chlorination is known method for killing undesirable microorganisms. Chlorine may be provided in multiple forms including chlorine gas ($Cl_2$), sodium hypochlorite liquid, calcium hypochlorite powder or granules, or isocyurantes. Chlorine gas ($Cl_2$) is a relatively cheap and highly effective antimicrobial agent; however, it is also a highly toxic and corrosive gas. Hypochlorites such as NaOCl or $Ca(OCl)_2$ are a much safer alternative, but are considerably more expensive that gaseous chlorine. Finally, hypochlorite solutions (i.e., bleach) may also be utilized, however these are rarely used in large scale water treatment applications because they are bulky and expensive. Regardless of the chlorine source, hypochlorous acid (HOCl) and the hypochlorite ion ($OCl^-$) are the final desirable antimicrobial products.

One method of forming HOCl occurs when $Cl_2$ is dissolved in water. The reaction proceeds according to the following equation:

$$Cl_2 + H_2O \Leftrightarrow HOCl + H^+ + Cl^- \quad (1)$$

Another method for producing HOCl uses metal hypochlorites dissolved in water. The reaction proceeds according to the following equation:

$$NaOCl + H_2O \Leftrightarrow NaOH + HOCl \quad (2)$$

This method is generally utilized by common household hypochlorites and generates HOCl on a relatively small scale.

HOCl is a weak acid and will dissociate. In aqueous solution, HOCl and $OCl^-$ are generally present in a pH dependent equilibrium:

$$HOCl \Leftrightarrow H^+ + OCl^- \quad pKa=7.53 \quad (3)$$

At low pH, HOCl is the predominant form, while at high pH, $OCl^-$ predominates. The HOCl form is about 80 times more effective than $OCl^-$ for killing microorganisms because HOCl crosses cell membranes easier than the hypochlorite ion. Accordingly, it would be desirable to control the pH of the chlorinated solution to increase the antimicrobial effectiveness of the chlorination process.

Processes and systems for adjusting the pH of a water stream are known in the art. U.S. Pat. No. 5,487,835 to Shane discloses a method and apparatus for controlling the pH of a water stream using carbon dioxide. Several methods currently are used to inject carbon dioxide into water. The most accepted method is to inject the carbon dioxide into the water by a direct gas feed through some type of diffusion system in a recarbonation basin; in effect, a bubbler. A mechanical mixer can be used in combination with this method for better efficiency. Another method for injecting carbon dioxide into water is to aspirate the carbon dioxide into a stream of water using a venturi type eductor. In this method, the carbon dioxide is injected into the stream of water and carried along with the stream of water to a grid system located in a basin or a pipeline.

Both the direct gas feed method and the venturi method of injecting carbon dioxide gas into water allow for the control of the pH and the stabilization of the treated water. However, it is difficult to control the efficiency of the carbon dioxide gas usage. Both of these processes require the use of a relatively large contact basin, a relatively long contact time or large amount of carrier water, all of which inherently are inefficient.

The formation of hypochlorous acid is also known in the art. For example, U.S. Pat. No. 4,017,592 to Penard et al. discloses a process for producing aqueous hypochlorous acid solution using a gas, liquid, solid phase system. U.S. Pat. No. 4,146,578 to Brennan et al. discloses a process for preparing hypochlorous acid wherein gaseous chloride is reacted with an aqueous solution of an alkali metal hydroxide in a finely divided mist at an elevated temperature to prevent condensation. U.S. Pat. No. 4,147,761 to Wojtowicz et al. discloses a hypochlorous acid process using a sweep reactor in which gaseous chloride is passed rapidly across the surface of an agitated aqueous solution of alkali metal hydroxide at a reduced temperature.

U.S. Pat. No. 4,190,638 to Hoekje et al. discloses the production of hypochlorous acid wherein a precipitate formed on a carbonating electrolytic cathode cell liquor is contacted in a fluidized bed with a mixture of gaseous chlorine and water vapor. The exit gas from the fluid vapor is absorbed in water. U.S. Pat. No. 4,504,456 to Yant et al. discloses a process and apparatus for forming hypochlorous acid by hydrolyzing chlorine with steam and water vapor and solid-gas stripping of the co-generated hydrochloric acid vapor. Hypochlorous acid vapor is dissolved into an aqueous product solution.

U.S. Pat. No. 5,037,627 to Melton et al. discloses a hypochlorous acid process by reacting an aqueous solution of an alkali metal hydroxide in droplet form with gaseous chlorine to produce hypochlorous acid vapor and solid alkali metal chloride particles. U.S. Pat. No. 5,322,677 to Shaffer et al. discloses a process for producing a concentrated aqueous hypochlorous acid solution by reacting droplets of an alkali metal hydroxide solution containing greater than 50 percent by weight of the alkali metal hydroxide with chlorine gas.

Despite the several known processes for producing hypochlorous acid, there remains a need for a quick, safe, and efficient process for producing hypochlorous acid solutions suitable for use as a disinfectant.

SUMMARY OF THE INVENTION

The present invention controls the hypochlorite/hypochlorous acid balance of a stream by mixing acid, preferably liquid acid, with a pressurized carrier stream which has been chlorinated by the addition of a chlorination agent. Preferably, all the streams are liquid streams. The introduction of the acid into the liquid stream reduces the pH of the liquid stream and increases the relative ratio of hypochlorous acid to hypochlorite of the liquid stream. The present invention discloses a novel hypochlorous acid forming process and system that are advantageous over other hypochlorous acid forming systems and processes because the pressurized streams of the present invention are readily manipulated to produce specific concentrations of hypochlorous acid thereby providing greater control over the reaction process. The hypochlorous acid solution formed using the present invention is suitable for use as a disinfectant in food processing, including but not limited to meat and poultry processing, treating wastewater, and treating drinking water.

In one embodiment, the system of the present invention takes a liquid acid and injects this acid into a chlorinated carrier water maintained at an elevated pressure. The lowering of the pH effectively converts the vast majority of the hypochlorite ions in the solution to its more highly effective hypochlorous acid form.

In yet another embodiment, the acid is a carbon dioxide-containing gas with a carrier liquid to form a carbon dioxide-water solution. This carbon dioxide-water solution is then injected into a liquid stream which has been chlorinated by the addition of a chlorination agent. The introduction of the carbon dioxide-water solution into the liquid stream causes the formation of carbonic acid therein, thereby reducing the pH of the liquid stream and increasing the relative ratio of hypochlorous acid to hypochlorite of the liquid stream.

The system of the present invention can take carbon dioxide gas at an elevated pressure and inject this gas into chlorinated carrier water, also at an elevated pressure. The chlorinated carrier water-carbon dioxide solution, still at an elevated pressure, then is injected into the water to be treated, which typically is at atmospheric pressure. As the pressurized carrier water-carbon dioxide solution is injected into the water to be treated, the carbon dioxide expands due to the lower pressure of the water to be treated and the excess carbon dioxide bursts forth out of solution as minute bubbles released into the main stream of water. The carbon dioxide bubbles mix rapidly with the main stream of water, thus reducing the pH of the main stream of water. In most cases, up to 95% of the chemical reaction between the main stream of water and the carbon dioxide gas is immediate, thus eliminating the need for a recarbonation basin or an extended contact area or contact time. The lowering of the pH also effectively converts a majority of the hypochlorite ion in the solution to a most highly effective hypochlorous acid form.

In another embodiment, the resulting hypochlorous acid solution of the present invention is greater than about 50%, more preferably about 77 to about 99 percent hypochlorous acid.

Accordingly, it is an object of the present invention to provide a solution feed system for injecting acid into a chlorinated water stream for reducing the pH of the water stream and increasing the concentration of hypochlorous acid therein.

It is yet a further object of the present invention to provide a solution feed system which can be operated continuously and eliminates the need for a batch treatment apparatus.

Another object of the present invention is to provide a solution feed system for controlling the pH of a chlorinated water stream which is efficient in operation, simple in construction and manufacture, and easy to operate.

It is an object of the present invention to provide a solution feed system for injecting carbon dioxide into a chlorinated water stream for controlling the pH of the water stream and increasing the concentration of hypochlorous acid therein.

Yet another object of the present invention is to provide a solution feed system in which recarbonation basins and/or extended contact areas or times are unnecessary.

A further object of the present invention is to provide a solution feed system in which elevated pressure carbon dioxide first is mixed with elevated pressure carrier water, and the elevated pressure carrier water-carbon dioxide solution then is injected into the water to be treated.

Still another object of the present invention is to provide a solution feed system in which carbon dioxide mixes almost immediately with the water to be treated, thus reducing the overall contact time needed between the carbon dioxide and the water to be treated.

These and other objects, features and advantages of the present invention will become more apparent upon reading the following specification in conjunction with the accompanying drawing figures.

DETAILED DESCRIPTION OF THE PREFERRED EMBODIMENT

Figure 1:
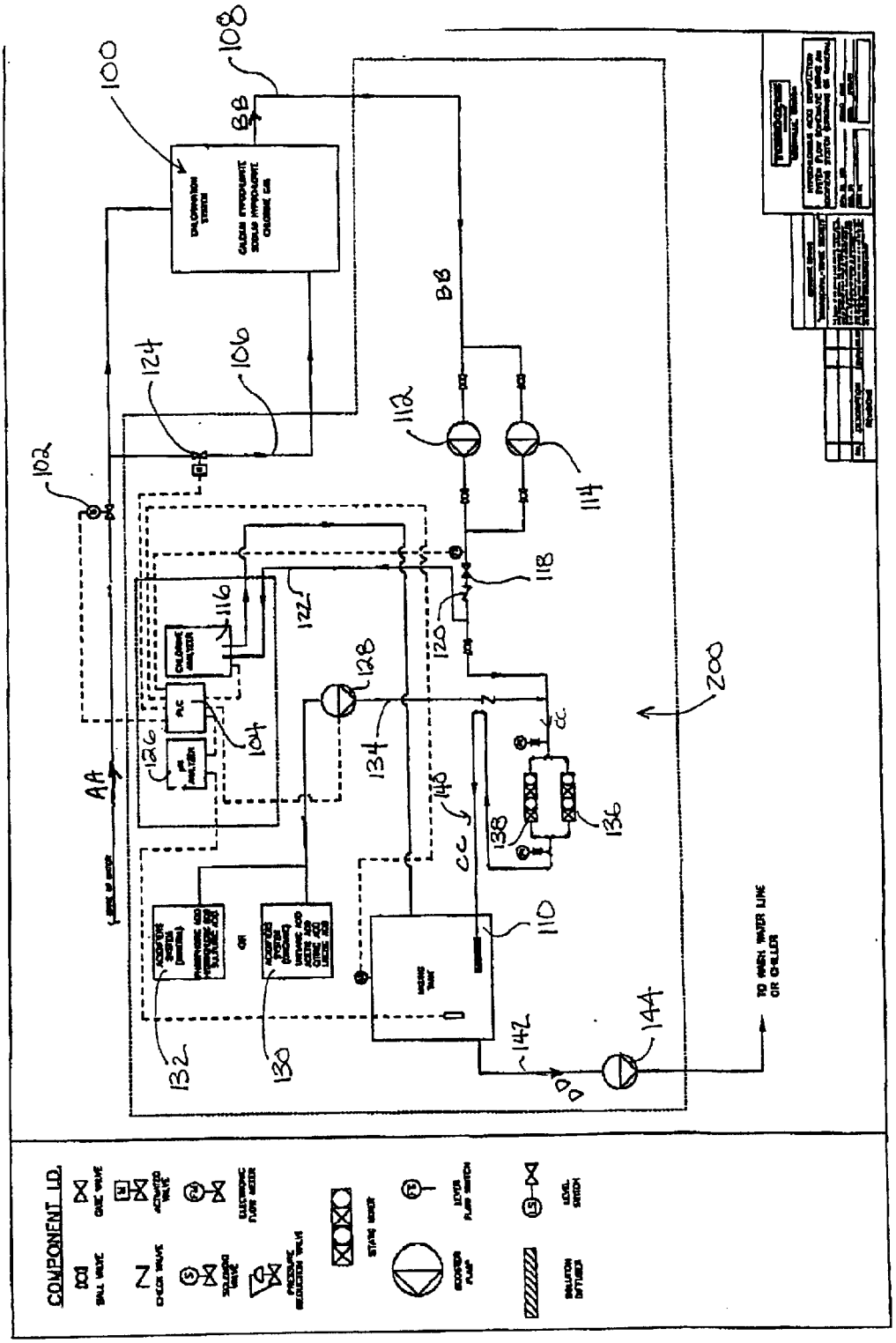
FIG. 1 is a flow diagram of a solution feed system in accordance with a preferred embodiment of the present invention.

Referring now to FIG. 1, a general schematic of the entire solution feed system is shown. In general, the solution feed system comprises a chlorination system 100, and an acid injection system 200. The various components of each of there systems are connected using standard piping. The hydrochlorous acid process of the present invention can be performed at ambient temperature or lower, i.e. about 25° C. or less.

As shown in FIG. 1, a stream of make up water AA is directed from a water source to chlorination system 100. Stream AA is typically maintained at normal line pressures. Stream AA flows through shut-off valve 102, and the total flow rate of make up water stream AA is controllable by, for example, the operation of a metering control valve 124 in response to signals from a Programmed Logic Controller (PLC) 104 which coordinates the overall system operation. A line 106 can split a portion of make up water stream AA providing greater control of the fluid volume in the chlorination system 100. The remainder of make up water stream AA enters chlorination system 100 and is subjected to chlorination therein by the addition of a chlorinating agent. The chlorinating agent may be a chlorine gas, a solid hypochlorite salt (e.g., NaOCl or $Ca(OCl)_2$), or a liquid hypochlorite solution (i.e., a bleach). The chlorination agent serves to raise the concentration of chlorine in make up water stream AA in the hypochlorite ion ($OCl^-$), hypochlorous acid (HOCl), or a combination thereof. In one embodiment, the chlorination agent is not a metal chlorite including but not limited to $NaOCl_2$.

Stream AA exits the chlorination system 100 as chlorinated stream BB through line 108 directed to a holding tank 110 through pumps 112 and 114 which increase the pressure of chlorinated water stream BB to at least about 50 psi. A small portion of chlorinated water stream BB can be diverted to a chlorine analyzer 116 from a point just downstream of gate valve 118 and check valve 120 via bypass stream 122. Gate valve 118 and check valve 120 prevent back flow in the system. Chlorine analyzer 116 can sense the chlorine level (ppm) of chlorinated water stream BB and transmits a signal indicative of this level to PLC 104. PLC 104 in turn generates a control signal operate metering control valve 124 to control the fraction of flow AA to maintain chlorinated water stream BB at a desired chlorine concentration. In one exemplary embodiment, the desired chlorine concentration is about 50 ppm or less.

A pH analyzer 126 can sense the pH of chlorinated water stream BB in holding tank 110 and communicates this information to PLC 104. PLC 104 regulates booster pump 128 such that the volume of acid from acidifier systems 130 or 132 increases to maintain the pH acidified chlorinated water stream/hypochlorous acid stream CC in the range of about 4.3 to about 7 resulting in an increase in HOCl concentration compared to OCl⁻ concentration in holding tank 110 (i.e., the ratio of HOCl to OCl⁻ is greater than one). Hypochlorous acid stream CC preferably contains about 77 to about 99 percent hypochlorous acid at ambient temperature.

The added acid can be organic or inorganic. Suitable organic acids include formic acid, acetic acid, citirc acid, lactic acid, trifluoroacetic acid, oxalic acid, tartaric acid, fumaric acid, maleic acid, methanesulfonic acid, benzenesulfonic acid and p-toluenesulfonic acid. Suitable inorganic acids include, but are not limited to, hydrochloric acid, hydrobromic acid, sulfuric acid, nitric acid and phosphoric acid. The acid stream joins chlorinated stream BB via line 134 upstream of static mixers 136 and 138. In one embodiment, hypochlorous acid stream CC is maintained at a pressure of at least 50 psi. It will be appreciated that the acids can be liquid or solid.

After acid injection, hypochlorous acid stream CC passes through the pair of static mixers 136 and 138 which are arranged in parallel and serve to evenly disperse the acid throughout the hypochlorous acid stream CC. Hypochlorous acid stream CC then optionally passes through a serpentine loop 140 which allows additional contact time for the injected acid to blend into hypochlorous acid stream CC.

Hypochlorous acid stream CC then enters holding tank 110 before injection into a target liquid stream DD via line 142. Pump 144 moves stream DD out of line 142 optionally to a wash water line or a chiller. In one embodiment, stream DD is maintained at a pressure of at least about 50 psi.

The pH analyzer 126 is provided to sense the pH of target liquid stream DD downstream of the point at which the acidified chlorinated carrier water is injected and to provide a signal indicative of the sensed pH to PLC 104. PLC 104 then adjusts the acid flow rate through pump 128 to control the amount of acid being introduced and thereby maintains the pH of target liquid stream DD at a desired setpoint for efficient chlorination as discussed above.

Figure 2:
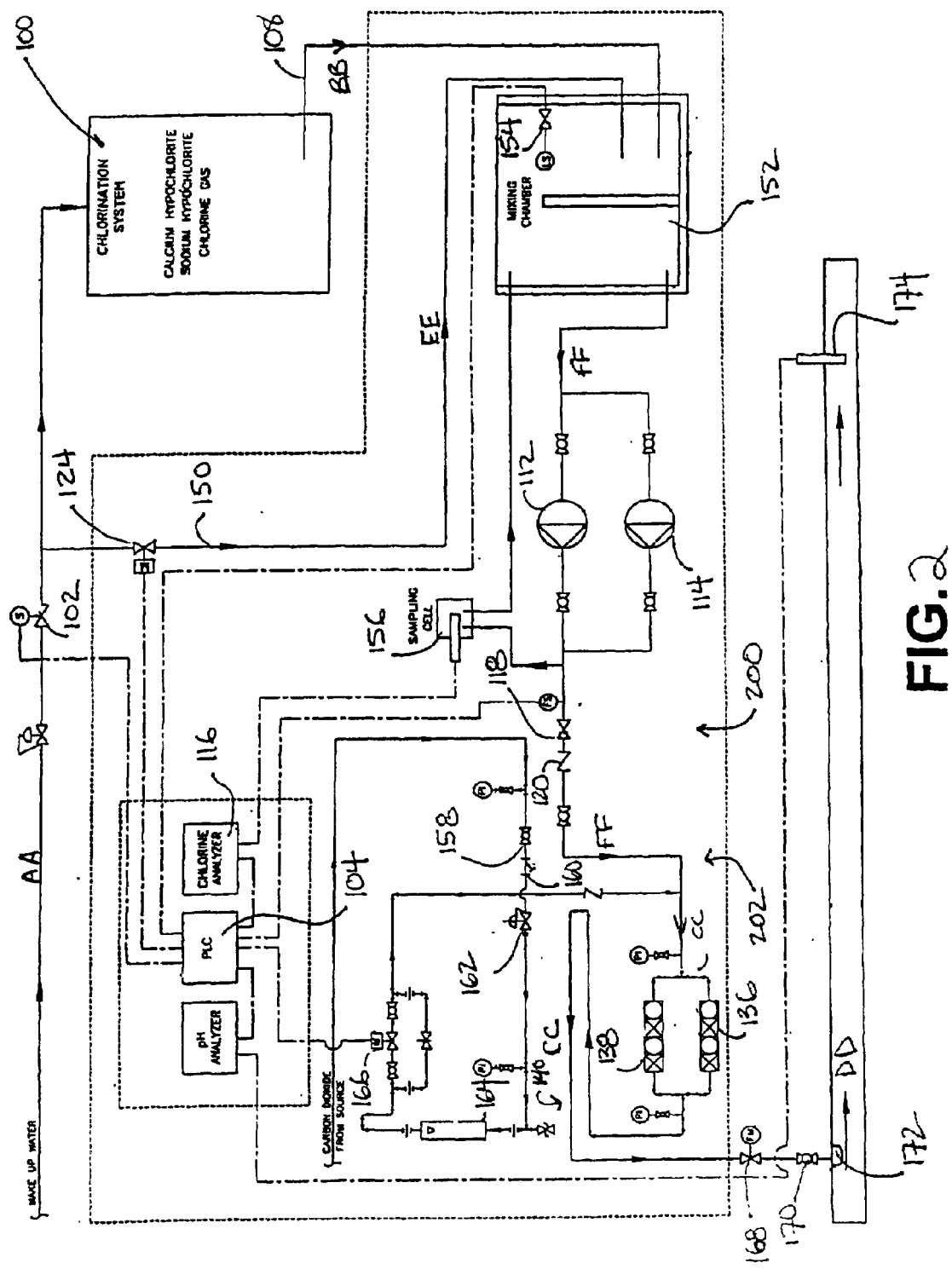
FIG. 2 is a flow diagram of a solution feed system in accordance with another preferred embodiment of the present invention.

In another preferred embodiment of the present invention utilizing a carbon dioxide injection system, as shown in FIG. 2, the stream of make up water AA is directed from a water source to the chlorination system 200. The description of the preferred embodiment of FIG. 1 is not repeated here, as only the differences between the two embodiments are highlighted. It will be understood by those of skill in the art that similar elements of FIGS. 1 and 2 perform the same or similar functions.

In this embodiment, a bypass line 150 diverts a portion of make up water stream AA around chlorination system 100 as a chlorination bypass stream EE. The remainder of make up water stream AA enters chlorination system 100 and is subjected to chlorination therein by the addition of a chlorinating agent. Stream AA exits the chlorination system 100 as chlorinated stream BB through line 108.

Bypass stream EE and chlorination stream BB are both directed into a mixing chamber 152 wherein they are recombined. Mixing chamber 152 includes a level sensor 154 which generates a signal indicative of the water level therein. This signal is relayed to PLC 104 which in turn generates a control signal to control the operation of flow control valve 102 to maintain a desired liquid level in mixing tank 152. Mixing tank 152 is sized to allow time for even mixing of the chlorinated subfraction of chlorination stream BB with bypass stream EE before allowing it to exit as mixed water stream FF.

Mixed water stream FF is directed from mixing chamber 152 through pumps 112 and 114. A small portion of mixed water stream FF can be diverted to a sampling cell 156, or directly to chlorine analyzer 116. Chlorine analyzer 116/ Sampling cell 156 can sense the chlorine level (ppm) of mixed water stream FF and transmit a signal indicative of this level to PLC 104. PLC 104 in turn generates a control signal operate metering control valve 102 to control the fraction of flow BB which passes through bypass line 150 to maintain mixed water stream FF at a desired chlorine concentration.

Mixed water stream FF next passes to acid injection system 200 being a carbon dioxide injection system 202 through gate valve 118 and check valve 120. In its simplest form, carbon dioxide injection system 202 includes a regulated flow of pressurized $CO_2$ which is injected into mixed water stream FF at a pressure significantly higher than that of mixed water stream FF. In one preferred embodiment, the carbon dioxide gas is directed through an isolation ball valve 158 then a wye strainer 160, then a pressure reduction valve 162. After pressure reduction valve 162, the carbon dioxide gas goes through a flow meter 164 and a $CO_2$ metering control valve 166 that is responsive to maintain the $CO_2$ flow at a desired rate as determined by PLC 104.

In a preferred embodiment, mixed water stream FF is maintained at greater than or equal to 50 psi at the $CO_2$ injection point and the $CO_2$ is maintained at a minimum of 55–75 psi or at least approximately 10 psi greater than the pressure of mixed water stream FF.

Hypochlorous acid stream CC then passes through a full port ball valve 170 before injection into a target liquid stream DD via diffuser 172. Diffuser 172 is designed to maintain system pressure, thus forcing the $CO_2$ gas to remain in solution in the hypochlorous acid stream CC.

In a preferred embodiment, the pressure of target liquid stream DD is less than that of the hypochlorous acid stream CC. Therefore, as the hypochlorous acid stream CC passes through the small holes in diffuser 172, it is diffused into target liquid stream DD, thereby lowering the pH of target liquid stream DD and shifting the hyopchlorite/ hypochlorous acid balance to form predominantly hypochlorous acid.

A pH sensor 174 can be provided to sense the pH of target liquid stream DD downstream of the point at which the hypochlorous acid stream CC is injected and to provide a signal indicative of the sensed pH to PLC 104. PLC 104 then adjusts the $CO_2$ flow rate through $CO_2$ metering valve 166 to control the amount of carbonic acid being introduced and thereby maintains the pH of target liquid stream DD at a desired setpoint for efficient chlorination as discussed above.

Figure 3:
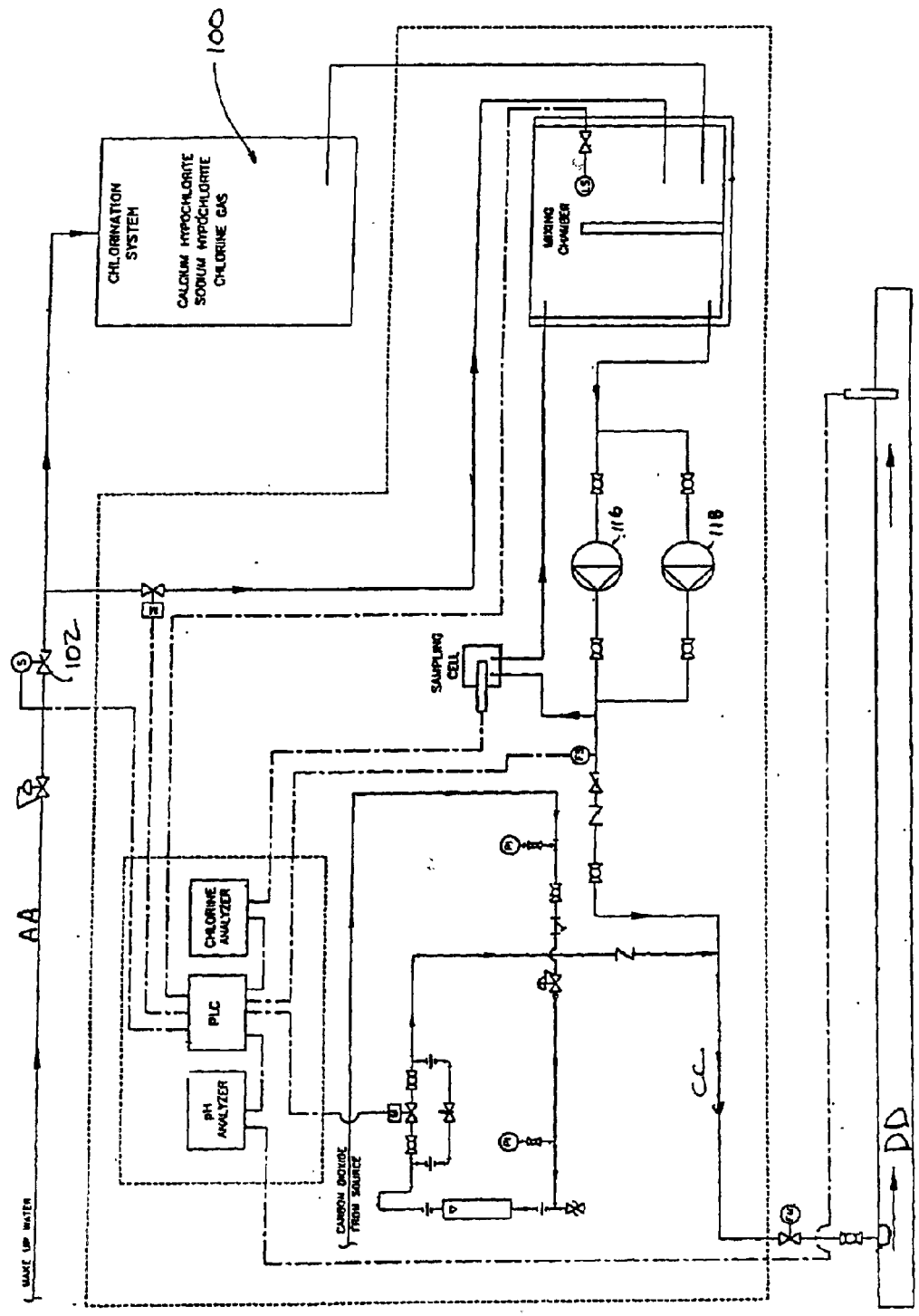
FIG. 3 is a flow diagram of a solution feed system in accordance with another preferred embodiment of the present invention.

As shown in FIG. 3, in an alternative embodiment, hypochlorous acid stream CC may also be added directly to target liquid stream DD immediately after injection of carbon dioxide gas. In this embodiment, the carbon dioxide gas will still be largely present in gaseous form because there are no static mixers or serpentine loop to provide additional mixing and time to allow the carbon dioxide to go into solution. A substantial portion of the carbon dioxide will still go into solution as carbonic acid in the target liquid stream as it flows to its end use.

As previously mentioned, in the treated water solution, HOCl and OCl⁻ are generally present in a pH dependent equilibrium:

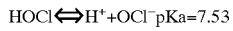

As shown in Table 1, at low pH, HOCl is the predominant form, while at high pH, OCl⁻ predominates:

TABLE 1

| pH\Temp °C. | \multicolumn{7}{c}{Percent HOCl} | | | | | | |
|---|---|---|---|---|---|---|---|
|  | 0 | 5 | 10 | 15 | 20 | 25 | 30 |
| 5.0 | 99.85 | 99.83 | 99.80 | 99.77 | 99.74 | 99.71 | 99.68 |
| 5.5 | 99.53 | 99.75 | 99.36 | 99.27 | 99.18 | 99.09 | 99.01 |
| 6.0 | 98.53 | 98.28 | 98.01 | 97.73 | 97.45 | 97.18 | 96.92 |
| 7.0 | 87.05 | 85.08 | 83.11 | 81.17 | 79.23 | 77.53 | 75.90 |
| 8.0 | 40.19 | 36.32 | 32.98 | 30.12 | 27.62 | 25.65 | 23.95 |
| 9.0 | 6.30 | 5.40 | 4.69 | 4.13 | 3.68 | 3.34 | 3.05 |
| 10.0 | 0.67 | 0.57 | 0.49 | 0.43 | 0.38 | 0.34 | 0.31 |
| 11.0 | 0.067 | 0.057 | 0.049 | 0.043 | 0.038 | 0.034 | 0.031 |

The HOCl is much more effective than OCl⁻ for killing microorganisms because HOCl is nonpolar and can cross the outer membrane of most microbes and bacteria. Therefore, it is desirable to control the pH of the treated water solution to between 4.3 and 7.0, and more preferable to between 6.0 and 6.2 in order to ensure almost complete (~98%) conversion to the hypochlorous acid form and thereby increase the antimicrobial effectiveness of the chlorination of the target liquid stream. At a pH of about 4.3 or lower, chlorine gas evolves from the solution. Therefore, in one embodiment, the pH of the solution stream is greater than about 4.3 to about 7.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for controlling the hypochlorite/hypochlorous acid balance of a fluid, the method comprising the steps of:

(a) acidifying a first carrier stream to form a first mixed stream;

(b) introducing a chlorination agent into a control stream, the chlorination agent increasing the concentration of hypochlorous acid and hypochlorite of the control stream;

(c) combining the first mixed stream with the control stream having the chlorination agent to form a third stream, thereby reducing the pH of the control stream having the chlorination agent and increasing the relative ratio of hypochlorous acid to hypochlorite of the third stream;

(d) monitoring chlorine levels and pH of the third stream; and (e) adjusting the first mixed stream and the control stream to maintain a desired hypochlorous acid level in the third stream.

2. The method according to claim 1, wherein the ratio of hypochlorous acid to hypochlorite in the third stream is greater than one.

3. The method according to claim 1, wherein the chlorination agent in the third stream is about 77 to about 99 percent hypochlorous acid.

4. The method according to claim 1, wherein the pH of the third stream is between approximately 4.3 and approximately 7.0.

5. The method according to claim 1, wherein the first mixed stream is pressurized.

6. The method according to claim 1, wherein the control stream with a chlorination agent is pressurized.

7. The method according to claim 1, wherein the first mixed stream is acidified with carbon dioxide.

8. The method according to claim 1, wherein the first carrier stream is pressurized to at least about 50 psi.

9. The method according to claim 1, wherein the chlorination agent is selected from the group consisting of chlorine gas, a solid hypochlorite salt, and a liquid hypochlorite solution.

10. The method according to claim 1, wherein the first mixed stream is acidified with an organic acid selected from the group consisting of formic acid, acetic acid, citirc acid, lactic acid, trifluoroacetic acid, oxalic acid, tartaric acid, fumaric acid, maleic acid, methanesulfonic acid, benzenesulfonic acid and p-toluenesulfonic acid.

11. The method of claim 1, wherein the first mixed stream is acidified with an inorganic acid selected from the group consisting of hydrochloric acid, hydrobromic acid, sulfuric acid, nitric acid and phosphoric acid.

12. A method for controlling the hypochlorite/hypochlorous acid balance of a control stream, the method comprising the steps of:

(a) combining carbon dioxide with a pressurized first carrier stream to form a first mixed stream;

(b) introducing a chlorination agent into the control stream, the chlorination agent increasing the concentration of hypochlorous acid and hypochlorite of the control stream;

(c) combining the first mixed stream with the control stream having the chlorination agent to form a third stream, thereby reducing the pH of the control stream and increasing the relative ratio of hypochlorous acid to hypochlorite of the third stream;

(d) monitoring chlorine levels and pH of the third stream;

(e) adjusting the first mixed stream and the control stream to maintain a desired chlorine level and pH in the third stream.

13. The method of claim 12, wherein the first mixed stream comprises carbonic acid.

14. The method of claim 12, wherein the carbon dioxide is over approximately 55 psi.

15. The method of claim 12, wherein the first carrier stream is over approximately 10 psi.

16. The method of claim 12, wherein the carbon dioxide is at a first pressure, wherein the first carrier steam is at a second pressure and comprises water, wherein the first mixed stream is a carbon dioxide-water solution at a third pressure, wherein the control stream prior to introducing the chlorination agent has a fourth pressure and a first pH, and wherein the first, second and third pressures are each at least approximately 50 psi greater than the fourth pressure.

17. The method according to claim 16, wherein the first pressure is between about 55 psi and 75 psi and the second pressure is greater than about 10 psi.

18. The method according to claim 16, wherein the chlorination agent is selected from the group comprising: chlorine gas, a solid hypochlorite salt, and a liquid hypochlorite solution.

* * * * *